(12) United States Patent
Lee et al.

(10) Patent No.: US 10,104,881 B2
(45) Date of Patent: Oct. 23, 2018

(54) COMPOSITION COMPRISING PLANT-DERIVED RECOMBINANT HUMAN SERUM ALBUMIN, LIPIDS, AND PLANT PROTEIN HYDROLYSATES AS ACTIVE INGREDIENTS FOR CRYOPRESERVATION OF STEM CELLS OR PRIMARY CELLS

(71) Applicant: CEFO Co., Ltd., Seoul (KR)

(72) Inventors: Sunray Lee, Seoul (KR); Jin Yup Lee, Seoul (KR); Hyun Jung Mo, Gyeonggi-do (KR); Hyun-Sook Park, Seoul (KR)

(73) Assignee: CEFO CO., LTD., Seoul (KR)

( * ) Notice: Subject to any disclaimer, the term of this patent is extended or adjusted under 35 U.S.C. 154(b) by 159 days.

(21) Appl. No.: 14/431,621

(22) PCT Filed: Sep. 27, 2012

(86) PCT No.: PCT/KR2012/007820
§ 371 (c)(1),
(2) Date: Mar. 26, 2015

(87) PCT Pub. No.: WO2014/051173
PCT Pub. Date: Apr. 3, 2014

(65) Prior Publication Data
US 2015/0327537 A1    Nov. 19, 2015

(51) Int. Cl.
| *A01N 1/02* | (2006.01) |
| *C12N 5/07* | (2010.01) |
| *C12N 5/0735* | (2010.01) |

(52) U.S. Cl.
CPC ......... *A01N 1/0221* (2013.01); *A01N 1/0284* (2013.01); *C12N 5/06* (2013.01); *C12N 5/0606* (2013.01)

(58) Field of Classification Search
None
See application file for complete search history.

(56) References Cited

U.S. PATENT DOCUMENTS

2012/0021510 A1* 1/2012 Hegel ................. C12N 5/0043
435/358

FOREIGN PATENT DOCUMENTS

| KR | 10-1999-0087669 | 12/1999 | |
| KR | 10-2010-0123995 | 11/2010 | |
| WO | WO 2007-146344 | 12/2007 | |
| WO | WO 2008009641 A1 * | 1/2008 | .......... C12N 5/0037 |
| WO | WO 2011-091350 | 7/2011 | |

OTHER PUBLICATIONS

Freshney, "Chapter 19:Cryopreservation", in Culture of Animal Cells: A Manual of Basic Technique and Specialized Applications, Sixth Edition, (2010), John Wiley & Sons, Inc., Hoboken, NJ, USA, doi: 10.1002/9780470649367.ch19 (Year: 2010).*
Hreinsson, et al., "Cryopreservation of follicles in hurrian ovarian cortical tissue. Comparison of serum and human serum albumin in the cryoprotectant solutions", Human Reproduction vol. 18, No. 11 pp. 2420-2428, 2003.

* cited by examiner

*Primary Examiner* — Robert J Yamasaki
*Assistant Examiner* — Charles Zoltan Constantine
(74) *Attorney, Agent, or Firm* — Cesari and McKenna, LLP

(57) ABSTRACT

The present invention relates to a composition including plant-derived recombinant human serum albumin, lipids, and plant protein hydrolysates as active ingredients for cryopreservation of stem cells or primary cells, and use thereof, more particularly, to a composition including plant-derived recombinant human serum albumin, lipids, and plant protein hydrolysates as active ingredients for cryopreservation of stem cells or primary cells, in which the albumin, lipids, and plant protein hydrolysates are present in sufficient quantities to reduce cell death caused by freezing while maintaining animal-free and xeno-free conditions during long-term preservation of stem cells or primary cells; and to a method for cryopreservation of stem cells or primary cells using the composition.

6 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220
```

```
Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
    355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
    515                 520                 525

Glu Thr Phe Thr Phe His Ala Asp Ile Cys Thr Leu Ser Glu Lys Glu
530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
    595                 600                 605

Leu

<210> SEQ ID NO 2
<211> LENGTH: 2264
<212> TYPE: DNA
<213> ORGANISM: Homo sapiens
```

<400> SEQUENCE: 2

```
agtatattag tgctaatttc cctccgtttg tcctagcttt tctcttctgt caaccccaca      60
cgcctttggc acaatgaagt gggtaacctt tatttccctt cttttctct ttagctcggc      120
ttattccagg ggtgtgtttc gtcgagatgc acacaagagt gaggttgctc atcggtttaa     180
agatttggga gaagaaaatt tcaaagcctt ggtgttgatt gcctttgctc agtatcttca     240
gcagtgtcca tttgaagatc atgtaaaatt agtgaatgaa gtaactgaat ttgcaaaaac     300
atgtgttgct gatgagtcag ctgaaaattg tgacaaatca cttcataccc ttttggaga     360
caaattatgc acagttgcaa ctcttcgtga aacctatggt gaaatggctg actgctgtgc     420
aaaacaagaa cctgagagaa atgaatgctt cttgcaacac aaagatgaca acccaaacct     480
cccccgattg gtgagaccag aggttgatgt gatgtgcact gcttttcatg acaatgaaga     540
gacattttg aaaaaatact tatatgaaat tgccagaaga catccttact tttatgcccc      600
ggaactcctt ttctttgcta aaggtataa agctgctttt acagaatgtt gccaagctgc      660
tgataaagct gcctgcctgt tgccaaagct cgatgaactt cgggatgaag ggaaggcttc     720
gtctgccaaa cagagactca gtgtgccag tctccaaaaa tttggagaaa gagcttttcaa     780
agcatgggca gtagctcgcc tgagccagag atttcccaaa gctgagtttg cagaagtttc     840
caagttagtg acagatctta ccaaagtcca cacggaatgc tgccatggag atctgcttga     900
atgtgctgat gacagggcgg accttgccaa gtatatctgt gaaaatcaag attcgatctc     960
cagtaaactg aaggaatgct gtgaaaaacc tctgttggaa aaatcccact gcattgccga     1020
agtggaaaat gatgagatgc ctgctgactt gccttcatta gctgctgatt ttgttgaaag    1080
taaggatgtt tgcaaaaact atgctgaggc aaaggatgtc ttcctgggca tgttttgta    1140
tgaatatgca agaaggcatc ctgattactc tgtcgtgctg ctgctgagac ttgccaagac    1200
atatgaaacc actctagaga agtgctgtgc cgctgcagat cctcatgaat gctatgccaa    1260
agtgttcgat gaatttaaac ctcttgtgga agagcctcag aatttaatca acaaaaattg    1320
tgagcttttt gagcagcttg gagagtacaa attccagaat gcgctattag ttcgttacac    1380
caagaaagta ccccaagtgt caactccaac tcttgtagag gtctcaagaa acctaggaaa    1440
agtgggcagc aaatgttgta acatcctga agcaaaaaga atgccctgtg cagaagacta    1500
tctatccgtg gtcctgaacc agttatgtgt gttgcatgag aaaacgccag taagtgacag    1560
agtcaccaaa tgctgcacag aatccttggt gaacaggcga ccatgctttt cagctctgga    1620
agtcgatgaa acatacgttc ccaaagagtt taatgctgaa acattcacct tccatgcaga    1680
tatatgcaca ctttctgaga aggagagaca aatcaagaaa caaactgcac ttgttgagct    1740
cgtgaaacac aagcccaagg caacaaaaga gcaactgaaa gctgttatgg atgatttcgc    1800
agcttttgta gagaagtgct gcaaggctga cgataaggag acctgctttg ccgaggaggg    1860
taaaaaactt gttgctgcaa gtcaagctgc cttaggctta taacatcaca tttaaaagca    1920
tctcagccta ccatgagaat aagagaaaga aaatgaagat caaaagctta ttcatctgtt    1980
ttcttttc gttggtgtaa agccaacacc ctgtctaaaa aacataaatt tctttaatca      2040
ttttgcctct tttctctgtg cttcaattaa taaaaaatgg aaagaatcta atagagtggt    2100
acagcactgt tatttttcaa agatgtgttg ctatcctgaa aattctgtag gttctgtgga    2160
agttccagtg ttctctctta ttccacttcg gtagaggatt tctagtttct tgtgggctaa    2220
ttaaataaat cattaatact cttctaaaaa aaaaaaaaa aaaa                     2264
```

COMPOSITION COMPRISING PLANT-DERIVED RECOMBINANT HUMAN SERUM ALBUMIN, LIPIDS, AND PLANT PROTEIN HYDROLYSATES AS ACTIVE INGREDIENTS FOR CRYOPRESERVATION OF STEM CELLS OR PRIMARY CELLS

CROSS REFERENCE TO RELATED APPLICATIONS

This application is the National Stage of International Application No. PCT/KR2012/007820, filed on Sep. 27, 2012, the content of which is hereby incorporated by reference in its entirety.

BACKGROUND OF THE INVENTION

Field of the Invention

The present invention relates to a composition including plant-derived recombinant human serum albumin, lipids, and plant protein hydrolysates as active ingredients for cryopreservation of stem cells or primary cells, and more particularly, to a composition including plant-derived recombinant human serum albumin, lipids, and plant protein hydrolysates as active ingredients for cryopreservation of stem cells or primary cells, in which the albumin, lipids, and plant protein hydrolysates are present in sufficient quantities to reduce cell death caused by freezing while maintaining animal-free and xeno-free conditions during long-term preservation of stem cells or primary cells; and to a method for cryopreservation of stem cells or primary cells using the composition.

Description of the Related Art

Stem cells refer to cells that can proliferate indefinitely in an undifferentiated state as well as differentiating to have a specialized function and shape when specific environments and conditions are provided. Since human embryonic stem cells are capable of continuous self-renewal and pluripotency like differentiating into all cell types of the human body, under appropriate in vitro culture conditions, the range of applications of studies on human embryonic stem cells are expanding to a wide variety of fields including basic studies for understanding development, differentiation, and growth of the human body, development of cell therapy products for the treatment of damages or various diseases of the human body, and efficacy screening for various candidate therapeutic drugs, disease etiology study, development of therapy strategies, etc. Even though demands for adult stem cells and human embryonic stem cells are rapidly increasing, there is an obstacle to development of the related technology because of a lack of techniques and methods for maintenance and long-term preservation of undifferentiated adult stem cells and human embryonic stem cells.

Further, primary cells refer to normal cells that are obtained by a direct primary culture of animal tissues or organs, directly obtained from living organisms. When these cells are cultured, they grow and go through cell divisions to a certain extent, but have a limitation as they undergo senescence after a certain number of passages. Despite such limitation, primary cells are still used in production of biomedical products due to an advantage of showing responses similar to those of a living organism. However, cryopreservation of cells is required because of the limitation.

Therefore, to use stem cells or primary cells in a clinical test, cell therapy, etc., it is very important to develop a preservation solution containing no animal-derived factors and a preservation method suitable for primary cells and stem cells, respectively.

Cold preservation and cryopreservation are representative methods for a method of preserving stem cells while maintaining their survival rate and characteristics such as pluripotency or multipotency. The cold preservation is a method of preserving stem cells at a low temperature, which was developed for the purpose of short-term transportation and storage. However, cold preservation method is suitable only for short-term preservation for 1 week or shorter, more accurately, 1 to 3 days at a low temperature (4° C.), and thus there is a limitation in use of cold preservation for long-term preservation of stem cells and primary cells. In contrast, cryopreservation is a method of preserving cells, tissues, and organs at an ultra-low temperature of −70° C. to −196° C., at which all metabolic processes in cells come to a halt, thereby semi-permanently preserving desired stem cells. This method is the most ideal method for semi-permanent preservation of stem cells and primary cells for research and therapeutic purposes, and is used for preservation of stem cells and primary cells in all nonprofit or commercial cell banks.

However, it is difficult to avoid cell damage caused by freezing and thawing processes which are inevitably accompanied by ice crystal formation and ionic and osmotic imbalance. Thus, there is increasing concern about the damage due to freezing and thawing processes. In order to minimize the damage and maximize survival rate and stemness after freezing and thawing processes, it is very important to develop cryopreservatives and cryopreservation methods according to biochemical and physical characteristics of corresponding cells for minimizing damages caused by freezing and thawing processes.

In general, intracellular ice crystallization which occurs during cryopreservation of animal cells is the main cause of cell damage. In order to prevent it, a cryoprotectant is used, and dimethyl sulfoxide (DMSO) or glycerol is mainly used. They are permeating-type cryoprotectants which effectively reduce ice crystallization during freezing and thawing processes. In detail, glycerol functions as a salt-buffer to bind to metal ions and to dehydrate cells themselves, thus inhibiting cell damage by reducing the volume of growing ice crystals during freezing of intracellular water. DMSO partially dissolves the cell membrane to prevent formation of a puncture and interferes with hydrogen bonding between water molecules to inhibit cell damage caused by ice crystals. However, there are still problems that cell damage is inevitable because DMSO and glycerol are cytotoxic, ionic and osmotic imbalance occurs, and active oxygen free radicals are generated during freezing and thawing processes.

Accordingly, in order to solve the problems to some extent, a method of combining cryoprotectants with a vehicle capable of minimizing ionic and osmotic imbalance and generation of active oxygen free radicals has been widely used. However, fetal bovine serum (FBS) or human serum which is generally used as a component of a cryopreservation liquid is also problematic in that their quality control is difficult, because of lot to lot variation, and that human-derived primary cells and stem cells to be stored can be exposed to infectious agents transmitted from animals (prion, virus, etc., which serves as the cause of bovine spongiform encephalopathy) or human serum, and may cause immune responses. To eliminate the problems of quality control of the cryopreservation liquid components and infectious agents, a technology using a recombinant human serum albumin produced from microorganisms or animal cells has been recently reported. However, the use of the recombinant human serum albumin also partially has the problem of quality control of cryopreservation liquid components, and risks of exposure to infectious agents which can infect animals still remains. Therefore, there is a need for development of new cryopreservation liquids.

Further, since kinds of components included in a cryopreservative composition and a composition ratio thereof may vary depending on types of cells to be cryopreserved, it is required to investigate components suitable for stem cells and primary cells and a proper composition ratio thereof for development of a composition for effective cryopreservation of stem cells and primary cells. In order to develop a composition for cryopreservation of stem cells or primary cells with both safety and stability, it is required to develop xeno-free and animal-free components which are effective for cryopreservation of stem cells and primary cells and a proper composition ratio thereof.

SUMMARY OF THE INVENTION

Technical Problem

In this regard, the present inventors have devoted efforts to develop animal-free and xeno-free substances which can be used for cryopreservation of stem cells and primary cells, and a method thereof. As a result, they completed the present invention upon finding that when a cryopreservative composition including plant-derived recombinant human serum albumin, lipids, and plant protein hydrolysates obtained from a plant transformant is used, stem cells and primary cells can be safely cryopreserved without being contaminated by heterologous proteins, damage due to freezing can be minimized upon thawing, and a cell survival rate after thawing can be improved compared to the existing cryopreservative compositions containing a bovine serum protein or microorganism-derived recombinant human serum albumin.

Technical Solution

An objective of the present invention is to provide a composition for cryopreservation of stem cells or primary cells including plant-derived recombinant human serum albumin, lipids, and plant protein hydrolysates as active ingredients.

Another objective of the present invention is to provide a method for cryopreservation of stem cells or primary cells using the composition.

BRIEF DESCRIPTION OF THE DRAWINGS

FIG. 4 shows microscopic images of bone marrow mesenchymal stem cells which were cryopreserved for 2 weeks using a cryopreservative (FBS) including fetal bovine serum (FBS), a cryopreservative (HSA) including microorganism-derived recombinant human serum albumin, and a cryopreservative (Plant protein/Lipid) of the present invention including plant-derived recombinant human serum albumin, lipids, and plant protein hydrolysates, thawed, and inoculated in a culture dish, followed by incubation for 1 day. The upper images were taken at 50× magnification and the lower images were taken at 100× magnification. When the composition of the present invention (Plant protein/Lipid) was used, healthier cells were observed, compared to when a cryopreservative including fetal bovine serum or microorganism-derived recombinant human serum albumin was used.

DETAILED DESCRIPTION OF THE PREFERRED EMBODIMENTS

In an aspect to achieve the above objectives, the present invention provides a composition for cryopreservation of stem cells or primary cells, including plant-derived recombinant human serum albumin, lipids, and plant protein hydrolysates as active ingredients.

Since the composition for cryopreservation of the present invention includes plant-derived recombinant human serum albumin, lipids, and plant protein hydrolysates without animal-derived factors, xeno-free condition may be maintained and thus risks of infection by a prion protein, etc. is low during preservation of stem cells or primary cells, thereby enabling a safe use thereof. Further, a composition includes components that exhibit strong effects on cryopreservation of stem cells or primary cells, thereby effectively reducing cell death due to freezing as well as stably maintaining characteristics of primary cells or stem cells, and thus it is very useful for long-term storage of the cells. A cryopreservative composition that includes all of the plant-derived recombinant human serum albumin, lipids, and plant protein hydrolysates of such effects, and a composition ratio thereof have not been reported yet and investigated by the present inventors for the first time. Furthermore, the cryopreservative composition consisting of a combination of the plant-derived recombinant human serum albumin, lipids, and plant protein hydrolysates is able to maintain functions of preserved cells and to remarkably increase cell survival rate upon thawing, compared to conventional cryopreservative compositions, thereby being usefully applied to cryopreservation of stem cells or primary cells which are needed for autologus therapy, etc.

As used herein, the term "cryopreservation" refers to stably maintaining cells for a long period of time via freezing. Generally, when cells are cultured, a mutation occurs in a ratio of one to ten thousands, and when cells go through a long-term subculture, cell populations change and become different from the original populations. In severe cases, cells may lose their own particular functions by subculture. Further, cells may be infected with mycoplasma, etc. during subculture. Because of such problems, cell cryopreservation is performed to freeze and preserve cells before losing their intrinsic characteristics, and to use them again when needed. In particular, if stem cells are used for therapy, it is necessary to be able to immediately use healthy stem cells when needed. Thus, effective cryopreservation is considered especially important for stem cells. Cryopreservation may be performed by a typical method of freezing and preserving cells well known in the art, such as a vitrification method, a slow freezing method or a mass cryopreservation method, without being limited thereto. With respect to the objectives of the present invention, a cryopreservation method includes any method without limitations, as long as it can effectively preserve stem cells or primary cells. In an embodiment of the present invention, a vitrification method and a slow freezing method were used (Example 3).

Cell cryopreservation may be performed by treating a cryportectant to cells to be cryopreserved, and various components may be additionally included to prevent cell damage due to a cryoprotectant. A cryopreservative composition of the present invention includes plant-derived recombinant human serum albumin (hHSA), lipids and plant protein hydrolysates, thereby improving safety and stability in cryopreservation of stem cells or primary cells.

As used herein, the term "plant-derived recombinant human serum albumin" refers to a protein that is obtained by transforming a plant cell with an amino acid sequence of the whole human serum albumin or a biologically active part of human serum albumin. The human serum albumin may be used in cryopreservation as an animal-free alternative which is equivalent or superior to serum, and may be added to a cryopreservative composition, thereby stabilizing cells. In particular, recombinant human serum albumin of the present invention is advantageous in that it is produced from a plant transformant, thereby minimizing risks for animal or viral infectious agents. Therefore, recombinant human serum albumin is useful for application of stem cells or primary cells, and in particular, for therapeutic purposes. Further, plant-derived recombinant human serum albumin included in the composition of the present invention is also advantageous in that it rarely exhibits lot to lot variation, unlike human serum albumin derived from animal cell or serum.

In the composition of the present invention, plant-derived recombinant human serum albumin may be included in an amount of 5 parts by weight to 50 parts by weight, preferably 10 parts by weight to 40 parts by weight, based on 100 parts by weight of the total composition, but is not limited thereto.

Information about human serum albumin used in the present invention may be available from a known database, such as GenBank of the National Center for Biotechnology Information (NCBI), and example thereof may be a protein (NM_000477) with Accession No. NP_000468, but is not limited thereto. Further, the human serum albumin may be a protein that is identified by an amino acid sequence of SEQ ID NO. 1, and may include any protein as long as the protein has an amino acid sequence having 70% or more, preferably 80% or more, more preferably 90% or more, much more preferably 95% or more, most preferably 98% or more similarity to the above sequence. The protein is practically included in the composition of the present invention, thereby exhibiting a biological activity to inhibit cell damage during cell freezing. Further, it is obvious that a protein variant having an amino acid sequence of which a partial sequence is deleted, modified, substituted, or added is also included in the scope of the present invention, as long as an amino acid sequence has a biological activity equivalent or corresponding to that of human serum albumin. Further, a polynucleotide encoding the human serum albumin is a nucleotide sequence of SEQ ID NO. 2. In addition, it is obvious that a nucleotide sequence having 70% or more, preferably 80% or more, more preferably 90% or more, much more preferably 95% or more, most preferably 98% or more similarity to the above sequence and encoding a protein having a biological activity to inhibit cell damage during cell freezing is also included in the scope of the present invention.

The plant-derived recombinant human serum albumin may be obtained after transformation using an expression vector containing a polynucleotide encoding human serum albumin, or commercially available plant-derived recombinant human serum albumin may be purchased.

As used herein, the term "vector" refers to an expression vector capable of expressing a desired protein in an appropriate host cell. An expression vector containing a polynucleotide encoding the human serum albumin refers to a recombinant polynucleotide molecule containing a polynucleotide encoding human serum albumin and a regulatory sequence operably linked thereto. It refers to a vector of which transformation into a plant is possible and which is able to express a desired protein in the plant, with respect to the objectives of the present invention. The plant expression vector is not limited to a particular type, as long as it contains a polynucleotide encoding the human serum albumin.

Further, as used herein, the term "transformation" means that DNA is introduced into a host cell so that DNA becomes replicable, either as an extrachromosomal element or by chromosomal integration. Thus, transformation is an artificial genetic alteration by introducing a foreign DNA into a host cell. The transformation method of the present invention may be performed by any transformation method, and easily performed by a conventional method known in the art.

A kind of plant transformation producing recombinant human serum albumin of the present invention is not particularly limited, as long as it is able to express human serum albumin. Example thereof may include a tobacco, rice or bean transformation. In an embodiment of the present invention, as rice-derived recombinant human serum albumins, rAlbumin ACF which is a plant-derived recombinant human serum albumin manufactured by Sheffield, and Cellastim which is a plant-derived recombinant human serum albumin manufactured by InVitria were used.

As used herein, the term "lipid" refers to an organic substance including fat, wax, sterol, fat-soluble vitamin, monoglyceride, diglyceride, triglyceride, phospholipid, etc., and has a property of being insoluble in water but soluble in organic solvents. With respect to the objectives of the present invention, the lipid is not particularly limited to a certain kind, as long as it functions to inhibit cell damage during cryopreservation of stem cells or primary cells. Examples thereof may include plant phospholipids such as soy lecithin, cholesterol, arachidonic acid, DL-a-tocopherol acetate, linoleic acid, linolenic acid, myristic acid, oleic acid, palmitoleic acid, palmitic acid or stearic acid. Preferably, the lipid may include a sterol, cholesterol, but is not limited thereto. In an embodiment of the present invention, a lipid concentrate containing cholesterol, arachidonic acid, DL-a-tocopherol acetate, linolenic acid, linoleic acid, myristic acid, oleic acid, palmitoleic acid, palmitic acid, stearic acid, Tween80 was used.

The lipids function to enter cell membrane to reduce membrane damage when the cell membrane is weakened upon cryopreservation. For example, the cell membrane is weakened by the penetration of a cryoprotectant such as DMSO. Especially, if cholesterol is included, a ratio of cholesterol/phospholipid may be increased to remarkably reduce cell membrane damage. The lipids may be included in an amount of 0.1 part by weight to 5.0 parts by weight, preferably 0.1 part by weight to 1.0 part by weight, based on 100 parts by weight of the total composition of the present invention, without being limited thereto.

In an embodiment of the present invention, a lipid concentrate containing cholesterol was used as a representative lipid. It was confirmed that when a cryopreservative composition further includes lipids in addition to human serum albumin, the survival rate of cryopreserved cells was remarkably increased (Example 4).

As used herein, the term "plant protein hydrolysate" refers to a substance containing amino acids or/and peptides, in which a substance containing amino acids or/and peptides are prepared by hydrolysis of plant proteins. The plant protein hydrolysates may be prepared by hydrolysis of plant proteins using a particular enzyme, etc., but are not limited thereto. With respect to the objectives of the present invention, the plant protein hydrolysates are not particularly limited to a certain kind, as long as it includes amino acids capable of reducing cell damage during cryopreservation of stem cells or primary cells. Examples thereof may be tobacco, rice, or bean protein hydrolysates. The plant protein hydrolysates may be used by direct hydrolysis of plant proteins using an enzyme, etc., or commercially available plant protein hydrolysates. In an embodiment of the present invention, hydrolyzed bean proteins were used as plant protein hydrolysates, and ULTRAPEP SOY or ULTRAPEP YE manufactured by Sheffield were purchased and used.

Further, the plant protein hydrolysates may be obtained by direct hydrolysis using an enzyme, etc., or by further purification. The plant protein hydrolysates may preferably include essential amino acids such as valine, leucine, isoleucine, methionine, threonine, lysine, phenylalanine, or tryptophan, and/or non-essential amino acids such as arginine, asparagine, glutamine, glycine, histidine, serine, tyrosine, and proline, but are not limited thereto.

The plant protein hydrolysates include essential amino acids or/and non-essential amino acids which may be used as a basic energy source of cells, thus providing nutrients for cells, increasing their activity upon freezing and thawing, and thereby helping rapid recovery of the cells which contributes to an increase in cell survival rate. In an embodiment of the present invention, effects of plant protein hydrolysates were examined by using bean protein hydrolysates. As a result, it was confirmed that when a composition including plant-derived recombinant human serum albumin and lipids of the present invention further includes plant protein hydrolysates, survival rates of stem cells were remarkably increased, suggesting that addition of plant protein hydrolysates increases cryopreservation efficiency (Example 5).

In particular, when plant protein hydrolysates are included in an amount of 1 part by weight to 40 parts by weight, preferably 1 part by weight to 20 parts by weight, more preferably 1 part by weight to 10 parts by weight, based on 100 parts by weight of the total composition, cryopreservation efficiency may be maximized.

More preferably, the composition of the present invention may include 10 parts by weight to 40 parts by weight of plant-derived recombinant human serum albumin, 0.1 part by weight to 1 part by weight of lipids, and 1 part by weight to 10 parts by weight of plant protein hydrolysates, based on 100 parts by weight of the total composition, but is not limited thereto.

Further, the composition may further include a cryoprotectant.

As used herein, the term "cryoprotectant" refers to a substance that is used to minimize cell damage caused by freezing and thawing processes which are inevitably accompanied by ice crystal formation and ionic and osmotic imbalance when cells, tissues, or organs are preserved at an ultra-low temperature of −80° C. to −200° C. With respect to the objectives of the present invention, the cryoprotectant is not limited to a certain substance, as long as it is able to reduce cell damage during cryopreservation. Examples thereof may include a permeating-type cryoprotectant such as dimethyl sulfoxide (DMSO), glycerol, propylene glycol, ethylene glycol, etc., or a non-permeating-type cryoprotectant such as sucrose, carboxymethylcellulose salts, carboxymethylcellulose (CMC), monosaccharide, disaccharide, etc., but are not limited thereto. In an embodiment of the present invention, dimethyl sulfoxide (DMSO) was used as a representative cryoprotectant. The cryoprotectant may be included in an amount of 1 part by weight to 15 parts by weight, preferably 5 parts by weight to 10 parts by weight, based on 100 parts by weight of the total composition.

Furthermore, the composition of the present invention may further include one or more buffering agents selected from the group consisting of citrate, phosphate, succinate, tartrate, fumarate, gluconate, oxalate, lactate, acetate, histidine, and Tris, and one or more isotonic agents selected from the group consisting of sodium chloride, potassium chloride, boric acid, sodium borate, mannitol, glycerin, propylene glycol, polyethylene, glycol, maltose, sucrose, erythritol, arabitol, xylitol, sorbitol trehalose, and glucose. Further, a composition may include a cell death inhibitor such as a Rho associated kinase inhibitor, catalase, or zVAD-fmk.

A composition including the plant-derived recombinant human serum albumin, lipids, and plant protein hydrolysates of the present invention may be very usefully applied to cryopreservation of cells, especially, stem cells or primary cells.

As used herein, the term "stem cell" refers to an undifferentiated cell having self-renewal and differentiation capacity. Stem cells include subpopulations of pluripotent stem cells, multipotent stem cells, and unipotent stem cells according to their differentiation capacity. Pluripotent stem cells refer to cells that have potency to differentiate into all tissues or cells that constitute a living organism. Multipotent stem cells refer to cells that do not have potency to differentiate into all kinds but into plural kinds of tissues or cells. Unipotent stem cells refer to cells that have potency to differentiate into a particular tissue or cell.

Pluripotent stem cells may include embryonic stem cells (ES cells), embryonic germ cells (EG cells), induced pluripotent stem cells (iPS cells), etc. Multipotent stem cells may include adult stem cells such as mesenchymal stem cells (derived from fat, bone marrow, umbilical cord blood, or umbilical cord, etc.), hematopoietic stem cells (derived from bone marrow or peripheral blood), neural stem cells, germ stem cells, etc. Unipotent stem cells may include committed stem cells for hepatocytes, which are normally quiescent with low self-renewal capacity, but vigorously differentiate into hepatocytes under certain conditions. In an embodiment of the present invention, bone marrow mesenchymal stem cells and umbilical cord stem cells were used to examine that the composition of the present invention may be used for cryopreservation of stem cells with safety and stability.

Figure 9:
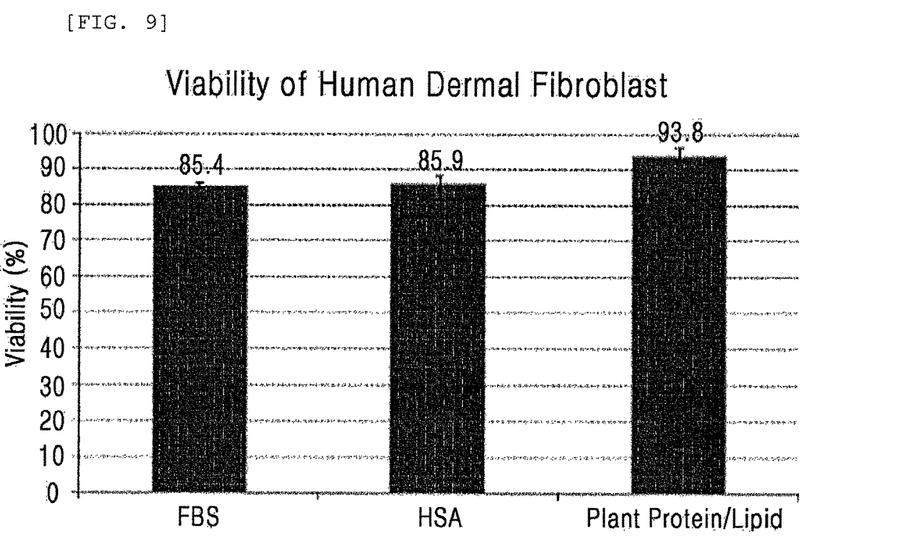
FIG. 9 is a graph of cell viability, in which human foreskin fibroblasts cells were cryopreserved for 2 weeks using a cryopreservative (FBS) including fetal bovine serum, a cryopreservative (HSA) including microorganism-derived recombinant human serum albumin, and a cryopreservative (Plant protein/Lipid) including plant-derived recombinant human serum albumin, lipids, and plant protein hydrolysates, and then thawed, followed by staining with propidium iodide (PI).

As used herein, the term "primary cell" refers to a cell that is isolated from a tissue of an individual without any genetic manipulation, etc., which represents functions of an organ/tissue of a living organism. Primary cells are isolated from skin or vascular endothelium, bone marrow, fat, cartilage, etc., and used for studying functions of corresponding tissues and cells, or as therapeutic agents for restoring lost tissues. In an embodiment of the present invention, foreskin-derived fibroblasts were used as representative primary cells to examine that the composition of the present invention may be used for cryopreservation of stem cells with safety and stability (FIG. 9).

The origins of the stem cells and primary cells are not particularly limited, as long as cells may be stably cryopreserved by the composition of the present invention. Examples thereof may include cells derived from human, monkey, pig, horse, cow, sheep, dog, cat, mouse, or rabbit. The stem cells or primary cells are preferably human stem cells or primary cells, but are not limited thereto.

Figure 3:
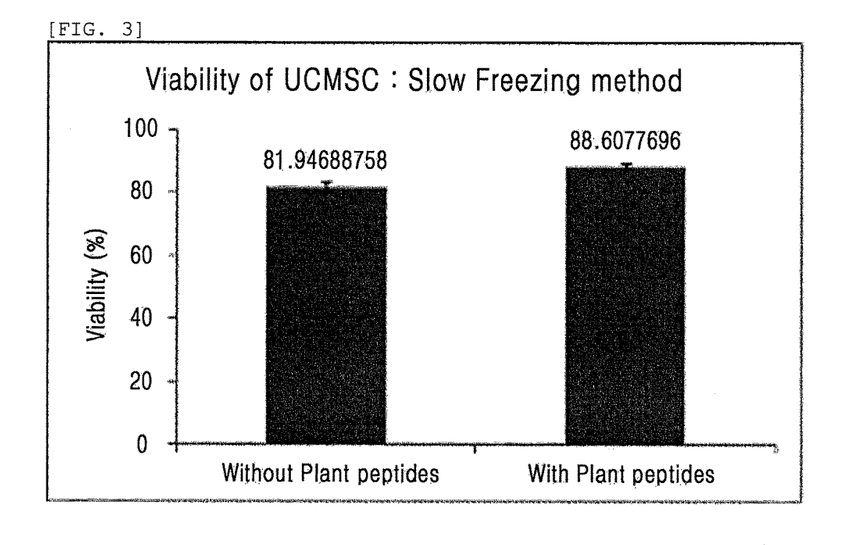
FIG. 3 shows effects of the composition of the present invention depending on addition of plant protein hydrolysates in order to examine effects of plant protein hydrolysates used in the composition of the present invention, in which a slow freezing method was used as a cryopreservation method. Umbilical cord-derived stem cells were cryopreserved using the method for 2 weeks, thawed, and stained with propidium iodide (PI) to examine cell viability. The results are demonstrated as a graph.

In an embodiment of the present invention, bone marrow mesenchymal stem cells and umbilical cord stem cells were used as stem cells, and human dermal fibroblast cells were used as primary cells. These cells were suspended in a cryopreservative composition including all of plant-derived recombinant human serum albumin, lipids, and plant protein hydrolysates of the present invention, frozen, thawed, and examined for cell viability and cell morphology. As a result, the composition of the present invention showed high cell viability and healthy morphology, compared to other conventional compositions including fetal bovine serum or microorganism-derived recombinant human serum albumin (FIGS. 4 to 7). In particular, when cells were cryopreserved by a slow freezing method, the composition of the present invention which further includes plant protein hydrolysates in addition to recombinant human serum albumin and lipids showed improved cell viability, compared to compositions including only recombinant human serum albumin and lipids, suggesting that the composition including all of the recombinant human serum albumin, lipids, and plant protein hydrolysates may be very stably used for cryopreservation of stem cells and primary cells (FIG. 3). In particular, since plant-derived human serum albumin, lipids, and plant protein hydrolysates included in the composition of the present invention are all derived from plants, they have animal-free and xeno-free conditions, thereby reducing risks of diseases transmitted from animals, such as bovine spongiform encephalopathy. Therefore, the composition of the present invention shows safety as well as stability.

In another aspect, the present invention provides a method for cryopreservation of stem cells or primary cells using the composition.

The composition, stem cells, primary cells and cryopreservation are as described above.

The cryopreservation method may include freezing stem cells or the primary cells which are treated with the composition, but is not limited thereto.

Freezing stem cells or primary cells that are treated with a cryopreservative composition of the present invention may be performed by a conventional method of freezing stem cells or primary cells known in the art, and examples thereof may include a vitrification method and a slow freezing method, but are not limited thereto. The vitrification method is performed by constantly decreasing a temperature at a rate of 1° C. per 1 minute using an apparatus such as a controlled-rate freezer (CRF). Preferably, when the temperature reaches −80° C., cells are immediately stored in a nitrogen tank. The slow freezing method may be performed by placing a vial containing a cryopreservative suspension containing cells in a freezer container box containing isopropyl alcohol, and by constantly decreasing the temperature for 12 hours to 24 hours in an ultra-low freezer at −70° C. or lower, without being limited thereto. Further, the frozen cells are stored in a liquid nitrogen tank, and used again when needed. In an embodiment of the present invention, stem cells and primary cells suspended in the composition of the present invention were frozen by a vitrification method and a slow freezing method, and stored in liquid nitrogen.

DETAILED DESCRIPTION OF THE EMBODIMENTS

Hereinafter, the present invention will be described in more detail with reference to Examples. However, these Examples 02 are for illustrative purposes only, and the invention is not intended to be limited by these Examples.

Example 1: Preparation of Stem Cells and Primary Cells

Bone marrow mesenchymal stem cells, umbilical cord matrix stem cells, and fibroblasts were directly extracted from the bone marrow, umbilical cord, and foreskin that were donated by patients, respectively. CB-MS-GM (CEFO., Seoul, Korea) was used as a culture medium for the stem cells, and CB-HDF-GM (CEFO., Seoul, Korea) was used as a culture medium for the fibroblasts. These cells were cultured in an incubator under conditions of 37° C. and 5% $CO_2$, and the culture medium was sustained by replacing it every 3 days.

All experiments of the present invention were approved by the Institutional Bioethics Review Board at Cefo Co., Ltd., and performed by procedures and methods in compliance with Bioethics and Safety Act.

Example 2: Preparation of Cryopreservative Composition Including Plant-Derived Recombinant Human Serum Albumin, Lipids, and Plant Protein Hydrolysates In order to produce a cryopreservative composition that is used to preserve stem cells and primary cells with safety and stability, the present inventors used plant-derived recombinant human serum albumin, lipids, and plant protein hydrolysates as active ingredients. As plant-derived recombinant human serum albumin, rice-derived recombinant human serum albumin, rAlbumin ACF which is plant-derived recombinant human serum albumin manufactured by Sheffield, or Cellastim which is plant-derived recombinant human serum albumin manufactured by InVitria was used. As lipids, a cholesterol lipid concentrate (Invitrogen) was used. As plant protein hydrolysates, UltraPep Soy (manufactured by Sheffield) was used.

As a basal medium, MS-GM (CEFO., Korea) for stem cells and CB-HDF-GM (CEFO., Seoul, Korea) for primary cells were used. In this experiment, plant-derived recombinant human serum albumin protein was contained at 10% to 40%, and especially at 40%, the highest effect was observed. In the composition of the present invention, if the content of plant-derived recombinant human serum albumin was 20%, the content of the plant protein hydrolysates was mostly 5%, and if the content of plant-derived recombinant human serum albumin was 10%, the content of plant protein hydrolysates was 10%.

The composition of a cryopreservative of the present invention which was prepared using the active ingredients is given in Table 1 below.

TABLE 1

Main composition of a cryopreservative composition of the present invention

| Basal Medium | Cryoprotectant | Serum & Nutrients | Other |
|---|---|---|---|
| MS-GM (CEFO., Korea) or CB-HDF-GM (CEFO., Seoul, Korea) | DMSO 5-15% | FBS 10-50% HAS 10-50% Plant-derived recombinant human serum albumin and Lipids 10-50% | — — Plant protein hydrolysates 1-20% |

Example 3: Freezing/Thawing of Stem Cells

The bone marrow mesenchymal stem cells, umbilical cord matrix stem cell, and fibroblasts cultured by the method of Example 1 were recovered, and washed with PBS (Phosphate-buffered saline). The cells were recovered and stained with propidium iodide (PI), and the number of cells was counted. Next, stem cells or fibroblasts were prepared at a density of $1\times10^6$ cells/ml, and respective cells were suspended in a cryopreservative including fetal bovine serum (FBS) as a main ingredient; a cryopreservative including microorganism-derived recombinant human serum albumin (HAS) as a main ingredient; and a cryopreservative including plant-derived recombinant human serum albumin (Plant Protein, rhAlbumin) and lipids of Example 2 as main ingredients.

Cell cryopreservation was performed by a slow freezing method and a vitrification method using a CRF (Controlled-Rate Freezer) in the following manner.

The slow freezing method was performed by placing a vial containing cells suspended in cryopreservatives in a freezer container box containing isopropyl alcohol, constantly decreasing the temperature for at least 12 hours in an ultra-low freezer at −70° C. or lower, and transferring the vial to a liquid nitrogen tank. The vitrification method using CRF was performed by placing a vial containing cells suspended in cryopreservatives in a CRF apparatus, and decreasing an internal temperature of the vial at a rate of 1° C. per minute to reach −180° C. When the temperature of the vial reached −80° C., the vial was immediately taken out, and transferred to and stored in a liquid nitrogen tank, LN2 tank.

Thawing of the frozen cells was performed as follows.

2 weeks after freezing, cryopreserved stem cells and primary cells were taken out and thawed as soon as possible in a water bath at 37° C. Then, the cell-containing vial was cleaned using 70% ethanol to remove contaminants. The cells were washed with PBS or a basal medium, and then inoculated in a culture plate, followed by incubation for 24 hours. The effects of the cryopreservative composition of the present invention were examined.

Example 4: Analysis of Effect of Lipids in Cryopreservation

In order to examine whether stem cell damage can be reduced during freezing/thawing by using a cryopreservative liquid including lipids as an active ingredient, human serum albumin and a lipid concentrate which do not contain artificially high amounts of lipids were used to prepare a cryopreservative composition as in the composition of Table 2 below.

TABLE 2

Composition of main active ingredients of cryopreservative liquid for analyzing effects of lipids

| Basal Medium | Cryoprotectant | Serum & Nutrients | Other |
|---|---|---|---|
| MS-GM (CEFO., Korea) | DMSO (dimethyl sulfoxide) 5-15% | Human Serum Albumin 5-50% Human Serum Albumin 5-50% | — Cholesterol Lipid Concentrate 0.1%-1% |

Further, a composition of the lipid concentrate is given in Table 3 below.

TABLE 3

Composition of lipid concentrate

| | Arachidonic acid | Cholesterol | DL-α-Tocopherol acetate | Linoleic acid | Linolenic acid | Myristic acid | Oleic acid | Palmitoleic acid | Palmitic acid | Pluronic ® F-68 | Stearic acid | Tween ® 80 |
|---|---|---|---|---|---|---|---|---|---|---|---|---|
| mg/L | 2 | 220 | 70 | 10 | 10 | 10 | 10 | 10 | 10 | 100,000 | 10 | 2,200 |

Figure 1:
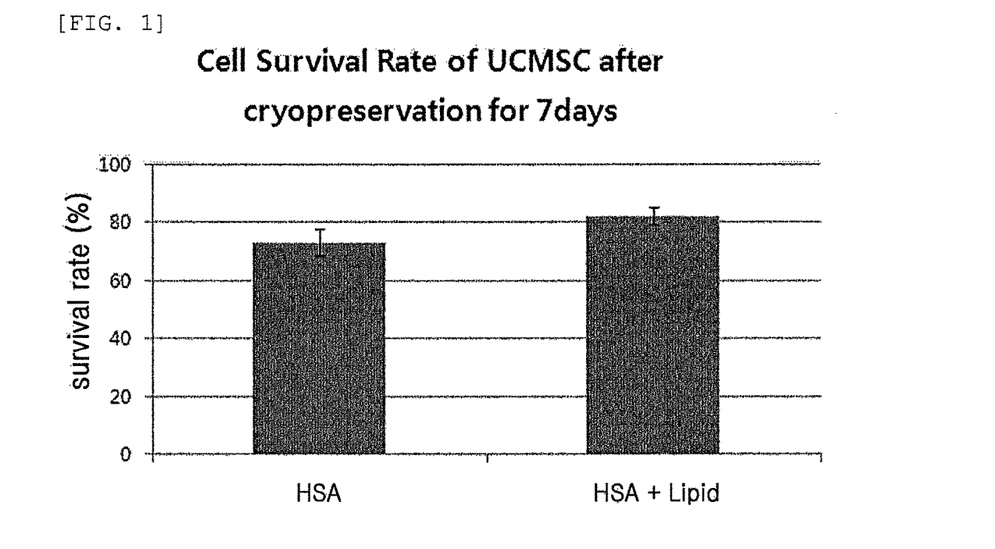
FIG. 1 shows cryopreservation effects a cryopreservative including recombinant human serum albumin (HSA) and a cryopreservative further including a lipid concentrate containing cholesterol (HSA+Lipid), in which umbilical cord mesenchymal stem cells were frozen using the respective cryopreservatives for 7 days and then thawed to examine their cell survival rates.
Figure 2:
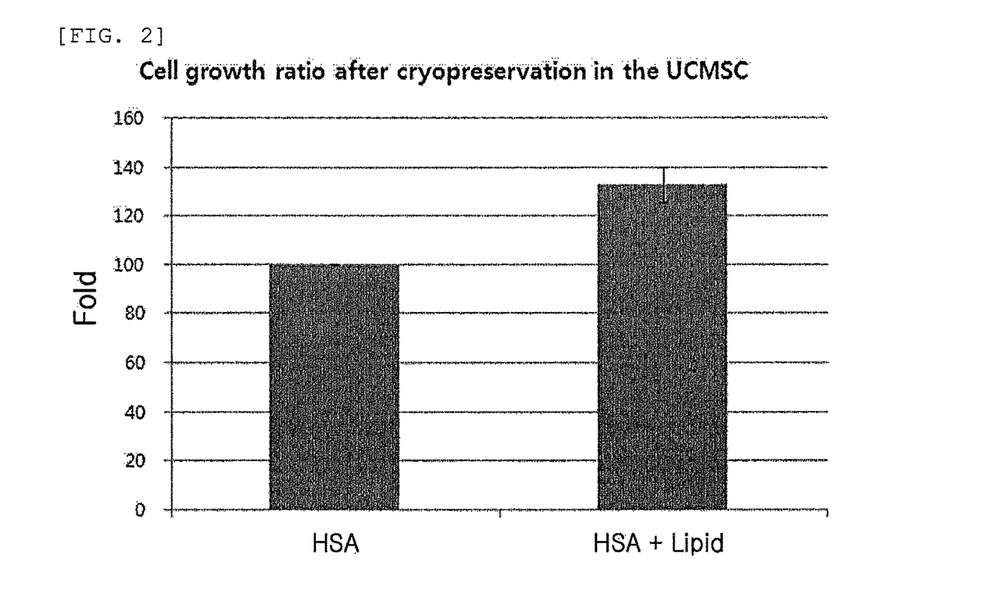
FIG. 2 shows cryopreservation effects of a cryopreservative including recombinant human serum albumin (HSA) and the cryopreservative further including a lipid concentrate containing cholesterol (HSA+Lipid), in which umbilical cord mesenchymal stem cells were frozen using the respective cryopreservatives for 7 days and then thawed, followed by incubation for 3 days and examination of cell growth ratios.

A cryopreservative liquid was prepared as in the composition of Table 2, and umbilical cord matrix stem cells (UCMSC) were suspended therein at a density of $1 \times 10^6$ cells/mL and frozen by a slow freezing method. Next, the cells were stored in the LN2 tank for 7 days, and then thawed to measure a cell survival rate. The results are shown in FIG. 1. Further, the thawed cells were inoculated in a 100 mm-culture plate, and cultured for 3 days. The number of cells was counted to examine cell survival rate, and the results are shown in FIG. 2.

As shown in FIG. 1, a cryopreservative composition including lipids in addition to albumin remarkably increased a cell survival rate by about 70% to 80% or higher. As shown in FIG. 2, when the cell survival rate of a cryopreservative composition including only human serum albumin was taken as 100, the cell survival rate of a cryopreservative composition further including lipids was 130 or higher.

These results suggest that a cryopreservative composition including lipids as active ingredients can be used to remarkably increase a cell survival rate, and a composition additionally including a lipid concentrate containing cholesterol, in particular, in a ratio of 0.1% to 1% is able to remarkably improve effects of cryopreservation of stem cells.

TABLE 4

Composition of main active ingredients of cryopreservative liquid for analyzing effects of plant protein hydrolysates

| Basal Medium | Cryoprotectant | Serum & Nutrients | Other |
|---|---|---|---|
| MS-GM (CEFO., Korea) | DMSO (dimethyl sulfoxide) 5-15% | rhAlbumin and lipids 5-50% | — |
| | | rhAlbumin and lipids 5-50% | Plant protein hydrolysates (Plant peptide I&II) 1-20% |

TABLE 5

Composition of plant protein hydrolysate consisting of Plant Peptide I & II

Plant Peptides I

| | Ala | Arg | Asn | Asp | Cys | Glu | Gly | His | Ile | Lys | Met | Phe | Pro | Ser | Thr | Trp | Tyr | Val |
|---|---|---|---|---|---|---|---|---|---|---|---|---|---|---|---|---|---|---|
| mg/g | 19.0 | 30.0 | — | 51.0 | — | 12.7 | 22.0 | 10.0 | 24.0 | 40.0 | 8.0 | 25.0 | 21.0 | 29.0 | 24.0 | — | 16.0 | 72.0 |

Plant Peptides II

| | Ala | Arg | Asn | Asp | Cys | Gln | Glu | Gly | His | Isl | Leu | Lys | Met | Phe | Pro | Ser | Thr | Trp | Tyr | Val |
|---|---|---|---|---|---|---|---|---|---|---|---|---|---|---|---|---|---|---|---|---|
| mg/g | 35.0 | 42.0 | — | 64.0 | — | — | 227.0 | 22.0 | 10.0 | 24.0 | 40.0 | 44.0 | 8.0 | 25.0 | 21.0 | 29.0 | 24.0 | — | 16.0 | 72.0 |

Example 5: Analysis of Effect of Plant Protein Hydrolysates in Cryopreservation

In order to examine whether damage of umbilical cord matrix stem cells due to freezing/thawing can be reduced by using a cryopreservative liquid further including plant protein hydrolysates in addition to plant-derived recombinant human serum albumin protein and lipids, a cryopreservative liquid was prepared as in the composition of Table 4 below.

In this regard, an amino acid composition of plant protein hydrolysates is given in Table 5 below, and as cells, umbilical cord matrix stem cells were used.

Umbilical cord matrix stem cells frozen by the slow freezing method of Example 3 were thawed, and stained with propidium iodide. The number of viable cells was counted using a cell counter to examine effects of plant protein hydrolysates on cell cryopreservation. The results are shown in FIG. 3.

As shown in FIG. 3, when cells were frozen by a slow freezing method frequently used in a laboratory, and then thawed, a composition further including plant protein hydrolysates in addition to plant-derived proteins and lipids showed about a 7 to 10% higher survival rate. Thus, the composition of the present invention further including plant protein hydrolysates particularly showed even greater cryopreservation effects when used in a slow freezing method.

These results suggest that the cryopreservative composition of the present invention further including plant protein hydrolysates can be usefully applied to cell cryopreservation. Based on these results, the present inventors produced a cryopreservative composition further including lipids and plant protein hydrolysates in addition to plant-derived recombinant human serum albumin protein, and they examined effects thereof on cryopreservation of stem cells and primary cells in the following Examples.

Example 6: Analysis of Effects of Plant-Derived Recombinant Human Serum Albumin, Lipids, and Plant Protein Hydrolysates on Cryopreservation of Bone Marrow Mesenchymal Stem Cells In order to examine effects of plant-derived recombinant human serum albumin, lipids, and plant protein hydrolysates included in the composition of the present invention on damage of bone marrow mesenchymal stem cells due to freezing/thawing, bone marrow mesenchymal stem cells which were frozen by the slow freezing method of Example 3 and then thawed were observed under a microscope, and the results are shown in FIG. 4.

Figure 5:
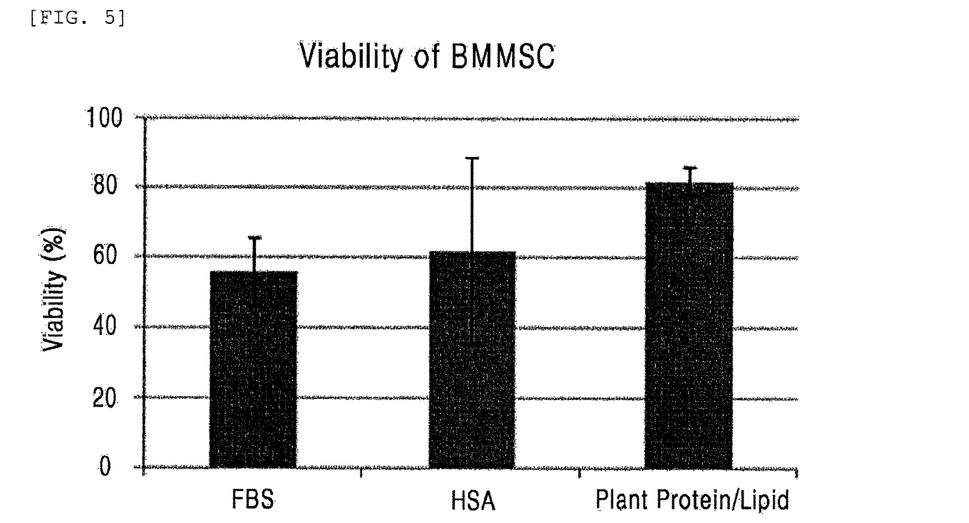
FIG. 5 is a graph from reanalysis of cell viability, in which bone marrow mesenchymal stem cells were cryopreserved for 2 weeks using a cryopreservative (FBS) including fetal bovine serum, a cryopreservative (HSA) including microorganism-derived recombinant human serum albumin, and a cryopreservative (Plant protein/Lipid) including plant-derived recombinant human serum albumin, lipids, and plant protein hydrolysates, and then thawed, followed by staining using propidium iodide.

Further, the cells were stained with a propidium iodide solution (Sigma, USA), and the number of viable cells was counted using a C-Chip Disposable Hemocytometer (Digital Bio., Korea) and a cell counter (Adam cell counter; Digital Bio., Korea). The results are shown in FIG. 5.

Figure 4:
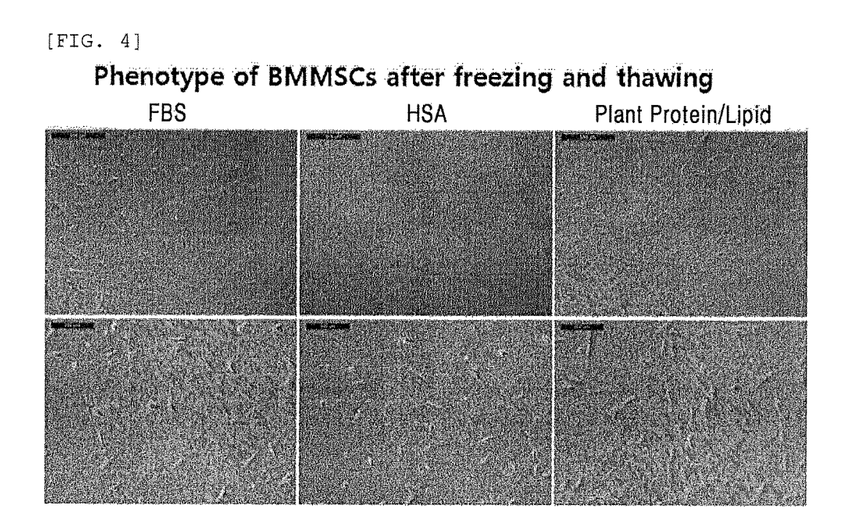

As shown in FIG. 4, when cryopreservation was performed using a cryopreservative composition of the present invention including all of plant-derived recombinant human serum albumin, lipids, and plant protein hydrolysates, after thawing and immediately culturing preserved cells in a culture dish, healthy stem cells were found at a higher density by morphological observation, compared to when a cryopreservative including fetal bovine serum or microorganism-derived recombinant human serum albumin was used. As shown in FIG. 5, when cryopreservation was performed using a cryopreservative composition of the present invention including plant-derived recombinant human serum albumin, lipids, and plant protein hydrolysates, after thawing, stem cells showed the highest viability of about 80%, compared to those of other experimental groups.

These results suggest that when a cryopreservative composition of the present invention including all of plant-derived recombinant human serum albumin, lipids, and plant protein hydrolysates is used, bone marrow mesenchymal stem cells can be cryopreserved without using animal-derived factors, and therefore, the stem cells can be preserved with safety and stability, compared to when conventional fetal bovine serum or microorganism-derived recombinant human serum albumin are used.

Example 7: Analysis of Effects of Plant-Derived Recombinant Human Serum Albumin, Lipids, and Plant Protein Hydrolysates in Cryopreservation of Umbilical Cord Matrix Stem Cells In order to examine effects of plant-derived recombinant human serum albumin, lipids, and plant protein hydrolysates on damage of umbilical cord matrix stem cells due to freezing/thawing, umbilical cord matrix stem cells which were frozen/thawed by the method of Example 3 were observed under a microscope, and the results are shown in FIG. 6.

Figure 7:
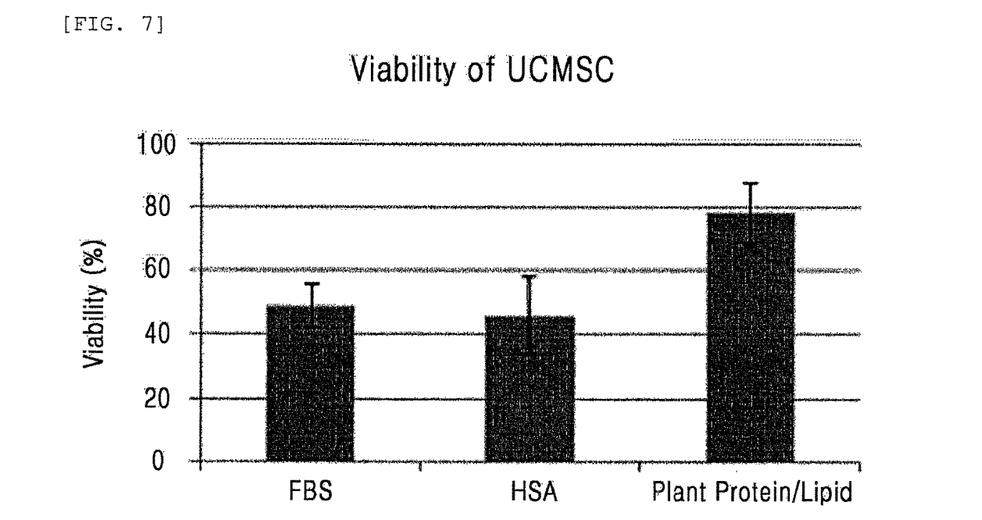
FIG. 7 is a graph of cell viability, in which umbilical cord matrix stem cells were cryopreserved for 2 weeks using a cryopreservative (FBS) including fetal bovine serum, a cryopreservative (HSA) including microorganism-derived recombinant human serum albumin, and a cryopreservative (Plant protein/Lipid) including plant-derived recombinant human serum albumin, lipids, and plant protein hydrolysates, and then thawed, followed by staining with propidium iodide, as in the condition for bone marrow mesenchymal stem cells.

Further, frozen/thawed umbilical cord matrix stem cells were stained with a propidium iodide solution (Sigma, USA), and the number of viable cells was counted using a C-Chip Disposable Hemocytometer (Digital Bio., Korea) and a cell counter (Adam cell counter; Digital Bio., Korea), and the results are shown in FIG. 7.

Figure 6:
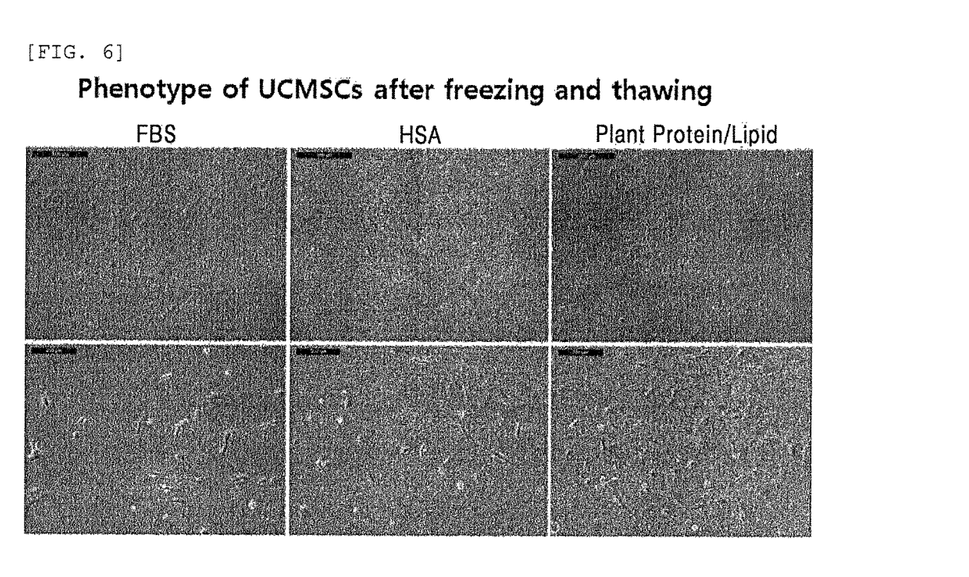
FIG. 6 shows microscopic images of umbilical cord matrix stem cell which were cryopreserved for 2 weeks using a cryopreservative including fetal bovine serum (FBS), a cryopreservative (HSA) including microorganism-derived recombinant human serum albumin, and a cryopreservative (Plant protein/Lipid) including plant-derived recombinant human serum albumin, lipids, and plant protein hydrolysates, thawed, and inoculated in a culture dish, followed by incubation for 1 day. The upper images were taken at 50× magnification and the lower images were taken at 100× magnification.

As shown in FIG. 6, when cryopreservation was performed using a cryopreservative composition of the present invention including all of plant-derived recombinant human serum albumin, lipids, and plant protein hydrolysates, after thawing and immediately culturing preserved cells, healthy stem cells were found at a higher density by morphological observation, compared when a cryopreservative including fetal bovine serum or microorganism-derived recombinant human serum albumin was used. As shown in FIG. 7, when cryopreservation was performed using a cryopreservative composition of the present invention including plant-derived recombinant human serum albumin, lipids, and plant protein hydrolysates and then thawing was performed, stem cells showed the highest viability of about 80%, compared to those of other experimental groups including fetal bovine serum or microorganism-derived recombinant human serum albumin.

Further, cells were frozen and thawed by a vitrification method, instead of a slow freezing method, and viability of umbilical cord matrix stem cells was examined. The results are shown in FIG. 8.

Figure 8:
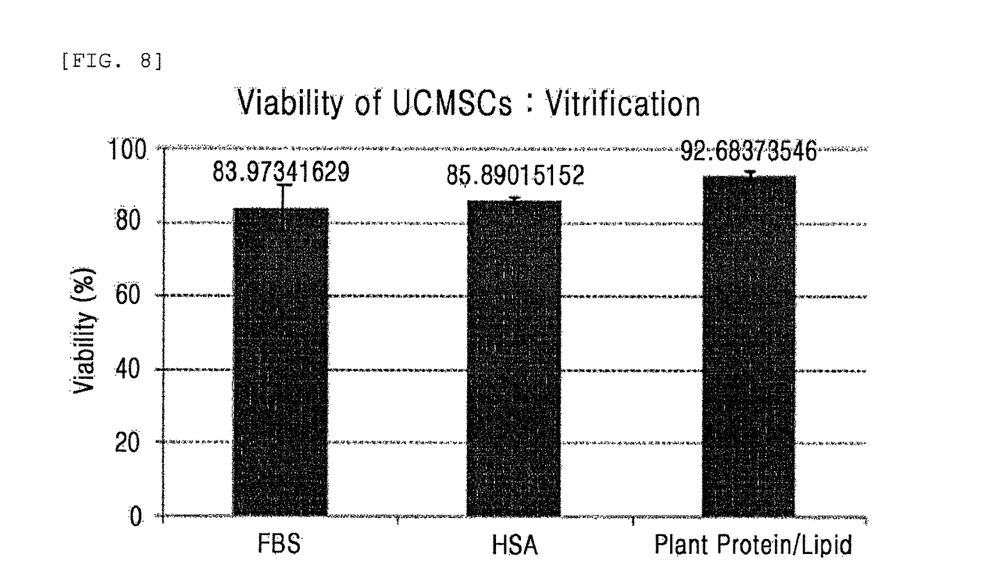
FIG. 8 is a graph of cell viability, in which umbilical cord-derived stem cells were cryopreserved by a vitrification method using a CRF apparatus and a cryopreservative (FBS) including fetal bovine serum, a cryopreservative (HSA) including microorganism-derived recombinant human serum albumin, and a cryopreservative (Plant protein/Lipid) including plant-derived recombinant human serum albumin, lipids, and plant protein hydrolysates, and immediately transferred to a LN2 Tank. The cells were stored for 2 weeks, and then thawed, followed by staining with propidium iodide (PI).

As a result, when a cryopreservative composition of the present invention including plant-derived recombinant human serum albumin, lipids, and plant protein hydrolysates was used, umbilical cord matrix stem cells showed viability of about 92% or higher, compared to when those of other cryopreservative compositions including fetal bovine serum or microorganism-derived recombinant human serum albumin are used (FIG. 8).

These results suggest that when a cryopreservative composition of the present invention including all of plant-derived recombinant human serum albumin, lipids, and plant protein hydrolysates is used, umbilical cord mesenchymal stem cells can be safely cryopreserved without using animal-derived factors, and it can also preserve with even greater safety and stability, compared to conventional fetal bovine serum or microorganism-derived recombinant human serum albumin.

Furthermore, these results taken together with the results of Example 6 suggest that a cryopreservative composition of the present invention including plant-derived recombinant human serum albumin, lipids, and plant protein hydrolysates can be used for cryopreservation of stem cells, independent of stem cell sources, and that it can thus allow long-term cryopreservation of stem cells, while maintaining xeno-free and animal-free conditions with safety and stability.

Example 8: Analysis of Effects of Plant-Derived Recombinant Human Serum Albumin, Lipids, and Plant Protein Hydrolysates in Cryopreservation of Human Dermal Fibroblasts In order to examine effects of plant-derived recombinant human serum albumin, lipids, and plant protein hydrolysates included in the composition of the present invention on damage of human dermal fibroblasts due to freezing/thawing, human dermal fibroblasts which were frozen/thawed by the slow freezing method of Example 3 were stained with a propidium iodide solution (Sigma, USA), and the number of viable cells was counted using a C-Chip Disposable Hemocytometer (Digital Bio., Korea) and a cell counter (Adam cell counter; Digital Bio., Korea). The results are shown in FIG. 9.

As shown in FIG. 9, when cryopreservation was performed using a cryopreservative composition of the present invention including plant-derived recombinant human serum albumin, lipids, and plant protein hydrolysates and then thawing was performed, human dermal fibroblasts showed the highest viability of about 93.8%, compared to those of other experimental groups including fetal bovine serum or microorganism-derived recombinant human serum albumin.

These results suggest that when a cryopreservative composition of the present invention including all of plant-derived recombinant human serum albumin, lipids, and plant protein hydrolysates is used, primary cells such as human dermal fibroblasts can be safely cryopreserved without using animal-derived factors, and it can also cryopreserve with even greater stability, compared to cryopreservative compositions including fetal bovine serum or microorganism-derived recombinant human serum albumin.

The results taken together with the results of Example 6 and Example 7 suggest that a cryopreservative composition of the present invention including plant-derived recombinant human serum albumin, lipids, and plant protein hydrolysates can be used for cryopreservation of primary cells as well as stem cells, and that it can thus allow long-term cryopreservation of stem cells and primary cells while maintaining xeno-free and animal-free conditions.

Based on the above description, it will be understood by those skilled in the art that the present invention may be implemented in a different specific form without changing the technical features or essential characteristics thereof. Therefore, it shall be understood that the above embodiments are not limitative, but illustrative in all aspects. The scope of the invention is defined by the appended claims rather than by the description preceding them, and therefore all changes and modifications that fall within metes and bounds of the claims, or equivalents of such metes and bounds are thus intended to be embraced by the claims.

EFFECT OF THE INVENTION

When a composition and a method of the present invention are used, stable cryopreservation is possible, because the survival rate of stem cells and primary cells can be maintained at high levels without using fetal bovine serum (FBS) or animal-derived factors, and safe human application thereof is also possible, because exposure to animal-derived infectious agents is prevented. Therefore, the composition and the method can be usefully applied to related pharmaceutical and medical industries that require animal-free and xeno-free conditions.

---

What is claimed is:

1. A composition for cryopreservation of stem cells or primary cells, comprising plant-derived recombinant human serum albumin, lipids, plant protein hydrolysate, and a cryoprotectant as active ingredients, wherein the stem cells are bone marrow mesenchymal stem cells or umbilical cord mesenchymal stem cells, the primary cells are fibroblasts, the cryoprotectant is selected from the group consisting of dimethyl sulfoxide, glycerol, propylene glycol, ethylene glycol, sucrose, carboxymethylcellulose salts, and carboxymethylcellulose, and the composition contains 40 parts by weight of plant-derived recombinant human serum albumin, 0.1 part by weight to 1 part by weight of lipids, and 1 part by weight to 10 parts by weight of plant protein hydrolysate, based on 100 parts by weight of the total composition.

2. The composition of claim 1, wherein the lipids contain cholesterol.

3. The composition of claim 1, further comprising a buffering agent or an isotonic agent.

4. A method for cryopreservation of stem cells or primary cells, comprising freezing stem cells or primary cells which are treated with a composition of claim 1, wherein the stem cells are bone marrow mesenchymal stem cells or umbilical cord mesenchymal stem cells and the primary cells are fibroblasts.

5. The method of claim 4, wherein the lipids contain cholesterol.

6. The method of claim 4, wherein the composition further comprises a buffering agent or an isotonic agent.

* * * * *